United States Patent [19]

Tournier et al.

[11] Patent Number: 4,900,931
[45] Date of Patent: Feb. 13, 1990

[54] DEVICE FOR LOCATING NUCLEAR RADIATION AND RADIATION IMAGE FORMATION DEVICE INCORPORATING SUCH A LOCATING DEVICE

[75] Inventors: Edmond Tournier, Grenoble; Michel Tararine, Sceaux, both of France

[73] Assignee: Commissariat a l'Energie Atomique, Paris, France

[21] Appl. No.: 192,777

[22] Filed: May 11, 1988

[30] Foreign Application Priority Data

May 27, 1987 [FR] France ................. 87 07482

[51] Int. Cl.⁴ ............................................. G01T 1/164
[52] U.S. Cl. ...................................... 250/369; 250/366
[58] Field of Search ................. 250/369, 366, 363 SG, 250/363, SE, 363 R, 363 SR

[56] References Cited

U.S. PATENT DOCUMENTS

| | | | |
|---|---|---|---|
| 3,011,057 | 11/1961 | Anger | 250/366 |
| 3,745,345 | 7/1973 | Muehllenhner | 250/363 R |
| 3,950,648 | 4/1976 | Mortone et al. | 250/369 |
| 4,060,730 | 11/1977 | Zioni et al. | 250/369 |
| 4,179,607 | 12/1979 | Lange et al. | 250/363 S |
| 4,223,388 | 9/1980 | Nishikawa et al. | 364/521 |
| 4,228,515 | 10/1980 | Genna et al. | 364/571.04 |
| 4,672,542 | 6/1987 | Roux et al. | 364/413.24 |

FOREIGN PATENT DOCUMENTS

| | | |
|---|---|---|
| 0021366 | 1/1981 | European Pat. Off. . |
| 2412856 | 7/1979 | France . |
| 2546633 | 11/1984 | France . |

Primary Examiner—Constantine Hannaher
Attorney, Agent, or Firm—Michael N. Meller

[57] ABSTRACT

Device for locating nuclear radiation and radiation image formation device incorporating such a locating device.

The locating device comprises a detection head having a crystal for converting a nuclear radiation into photons and a plurality of transducers for converting the photons into electric signals.

These signals are received in a position coder, which has in series a weighting circuit for supplying analog signals $X^+$, $X^-$, $Y^-$ (and optionally Z), a digitizing device for digitizing the analog signals and a digital computer for producing digital signals $X_N$, $Y_N$ defining the position of a nuclear radiation exciting the crystal.

8 Claims, 3 Drawing Sheets

DEVICE FOR LOCATING NUCLEAR RADIATION AND RADIATION IMAGE FORMATION DEVICE INCORPORATING SUCH A LOCATING DEVICE

DESCRIPTION

The present invention relates to a device for locating or localizing nuclear radiation. It also relates to a device for forming a radiation image incorporating such a locating device.

It more particularly applies to the medical field, where radiation image formation devices are used as a diagnosis aid. Such devices are generally referred to as scintillation cameras, gamma ray cameras or Anger cameras.

This application involves the administration by injection into a patient's vein of a small dose of radioisotope (a radioactive substance emitting gamma rays). The blood flow distributes the dose in the body and a transducer having an appropriate sensitivity records the development of this distribution.

The regions of the body having a large affinity for the isotope or a rich blood irrigation appear as bright or highly illuminated sources, whereas coversely the regions having a limited affinity or a limited blood irrigation appear dark. In this way, any part of the body or a specific organ can undergo reliable clinical investigation without involving surgery.

A gamma ray camera comprises a detection head generaly having a collimator for focusing the gamma rays emitted by the patient, a crystal for transforming the gamma photons into light photons or scintillations and a system of photomultiplier tubes for transforming each scintillation into an analog electrical pulse, also called electrical contribution.

It also comprises a positon coder for producing signals of coordinates X and Y of the point where a scintillation has occurred on the basis of analog electrical pulses supplied by the photomultiplier tubes. The detector head and the position coder together form a gamma radiation locating device.

A gamma ray camera also generally comprises a cathode-ray oscilloscope controlled by signals of coordinates X and Y and by a validation signal Z produced by the position coder on the basis of pulses supplied by the photomultiplier tubes, when the scintillation energy belongs to a predetermined energy band. Gamma radiation reaching the crystal is thus displayed as a light spot on the cathode-ray oscilloscope screen.

In order to produce a radiation image representing all the nuclear radiations received, a gamma ray camera can also incorporate a photographic apparatus for forming an image of the observed organ by the accumulation of a large number of light spots produced on the cathode-ray oscilloscope screen.

Finally, the display means can comprise a means for the digital processing of the images, particularly with a view to obtaining tomographs of the organ observed. In order to achieve this objective, several images of the organ are acquired in accordance with a plurality of observation orientations of the gamma ray camera with respect to said organ by signal processing operations like those encountered in tomoscanners, whereby it is possible to reconstitute images of sections of examined organs.

The detection head of a nuclear radiation locating device or a gamma ray camera has, by its very construction, at least two types of defect:

a spectrometry defect due to the drift of the gain of the photomultiplier tubes in time and to the non-uniformity of the detection sensitivity of said photomultiplier tubes;

a linearity defect due to geometrical distortions introduced by the photomultipliers.

These defects are corrected in two phases in per se known manner (cf. US-A-3745345, FR-A-2412856 and EP-A-0021366). In the first phase the state of the detection head with its defects is recorded and compared with an ideal detection head. This comparison makes it possible to calculate digital correction coefficients, which are stored in a memory. In the second phase the stored correction coefficients are applied to signals or coordinates X,Y supplied by the position coder. The signals of coordinates X,Y are consequently digitized in order to be combined with digital correction coefficients. The signals of coordinates X,Y supplied by the position coder when a gamma radiation reaches the crystal are produced in the following way.

It is known that a scintillation is simultaneously seen by several photomultiplier tubes, i.e. roughly 6 to 10 tubes. The determination of the location of the scintillation is obtained by calculating the location of the barycenter of the electrical contribution supplied by all the photomultiplier tubes excited by said scintillation.

This calculation is performed in conventional manner, as described in US-A-3011057, using several sets of electrical resistors, whose values are a function of the positions of the photomultiplier tubes to which they are connected. These positions are defined with respect to a reference mark of axes Ox and Oy. Within each set of resistors, there is one resistor per photomultiplier tube, each resistor being connected by one end to a photomultiplier tube and by another end to a common point. The signal supplied on said common point is consequently a weighting of the signals supplied by the photomultiplier tubes.

A position coder generally comprises four different sets of resistors supplying analog signals designated $X^+$, $X^-$, $Y^+$ and $Y^-$. It may optionally comprise a fifth set of resistors for supplying the validation signal Z representing the scintillation energy. The signals of coordinates X,Y are deduced, by an analog calculation, from the signals $X^+$, $X^-$, $Y^+$, $Y^-$ and possibly the signal Z.

The relations generally used for calculating the coordinate X are one of the following:

$$X = \frac{X^+ - X^-}{X^+ + X^-} \text{ or } X = \frac{X^+ - X^-}{X^+ + X^- + Y^+ Y^-} \text{ or } X = \frac{X^+ - X^-}{Z}$$

Symmetrical relations are used calculating the coordinate Y.

These calculations use analog dividers and it is necessary to standardize the signals $X^+$, $X^-$, $Y^+$, $Y^-$ as a function of the energy signal Z in order to place the divider in its linearity range.

The signals of coordinates X,Y obtained and the signal Z, if applicable, are then applied to the inputs of analog-digital converters for digitization.

This procedure suffers from the disadvantage of requiring analog-digital converters with an excellent differential linearity performance. Thus, if the amplitude range for the signals of coordinates X,Y is, for each analog-digital converter, broken down into segments of non-identical widths, certain digital values of the coordinates X,Y will be favored at the expense of other digital values.

Consideration will e.g. be given to the case of an analog signal, whose amplitude is approximately 0.99 and whose value is coded on two bits. A perfect analog-digital converter brings about correspondence of the logic value 00 with segment [0.24], logic value 01 with segment [25,49], logic value 10 with segment [50,74], and logic value 11 with segment [75,99], all the segments having the same length.

Conversely, an imperfect analog-digital converter e.g. associates the logic value 00 with segment [0.27], the logic value 01 with segment [28,49], the logic value 10 with segment [50,74] and the logic value 11 with segment [75,99]. Thus, an analog signal of amplitude coordinates 26 will be coded by the logic value 00 with the imperfect converter instead of being coded by the logic value 01 with the perfect coder. This leads to an error in the location of the scintillation.

In the same way, in the case of a radiation image formation device, a normally uniform radiation image will appear on the screen with rows or columns of higher or lower density than the mean value as a function of whether the segment associated with said row or column is wider or narrower than the mean value. Such a phenomenon is extremely visible, the eye being very sensitive to even slight contrast variations, if said variations have a geometrical shape.

The invention more particularly relates to obtaining signals of coordinates X,Y in digital form by means of analog-digital converters not necessary having at least great differential linearity.

The invention consists of digitizing the signals $X^+$, $X^-$, $Y^+$, $Y^-$ (and if applicable Z) and producing on the basis of the digitized signals signals of digital coordinates X,Y. In this way, the differential linearity of the analog-digital converters supplying the digital signals $X^+$, $X^-$, $Y^+$, $Y^-$ and Z is not a critical parameter, because in the final image the same signal of digital coordinate X is obtained by a large number of pairs of different digital signals $(X_N^+, X_N^-)$ corresponding to the statistical fluctuation of the energy of the scintillations.

More specifically, the invention relates to a device for locating a nuclear radiation incorporating a detection head for detecting a nuclear radiation and a position coder for locating said nuclear radiation, said detection head comprising a collimator, a planar layer of a material sensitive to said nuclear radiation for receiving on a first or front face a nuclear radiation traversing said collimator and for supplying on a second or rear face a light radiation which is a function of the nuclear radiation received, a plurality of transducers arranged on the rear face of said layer, each supplying an electric signal which is a function of the light radiation received, each nuclear radiation producing a light radiation seen by a plurality of transistors, said locating device being characterized in that the position coder comprises weighting means for supplying analog electric signals $X^+$, $X^-$, $Y^+$, $Y^-$, each representing weighted sums of the electric signal supplied by the transducers, the signals $X^+$, $X^-$ being a function of the position and the energy of the nuclear radiation received in accordance with an axis X and the signals $Y^+$, $Y^-$ being a function of the position of the nuclear radiation received in accordance with an axis Y, a digitizing means for receiving the analog signals $X^+$, $X^-$, $Y^+$, $Y^-$ and for supplying corresponding digital signals $X_N^+$, $X_N^-$, $Y_N^+$ and $Y_N^-$ and a calculating means or computer for determining the signals of digital coordinates $X_N$, $Y_N$ of the nuclear radiation received as a function of the digital signals $X_N^+$, $X_n^-$, $Y_N^+$ and $Y_N^-$.

The invention also relates to a radiation image formation device incorporating such a locating device and a display means incorporating a means for visualizing the image point of coordinates $X_N$, $Y_N$ and/or an imaging means for accumulating said image points.

The preferred embodiments of the invention will be described in greater detail hereinafter with reference to drawings, wherein:

FIG. 1 shows the display defect by prior art radiation image formation devices, when the analog-digital converters of the position coder have an even small differential non-linearity.

FIG. 2 diagrammatically shows the general structure of a nuclear radiation locating device.

Figure 9:
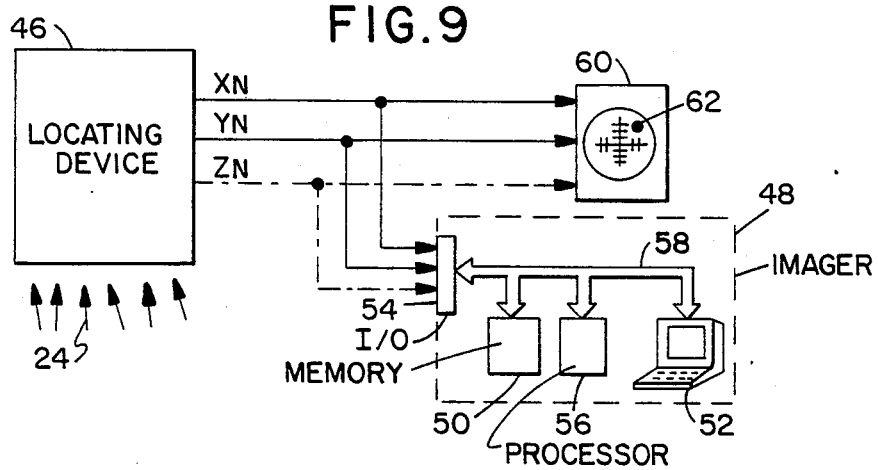

FIG. 9 diagrammatically depicts a radiation image formation device according to the invention.

Figure 1:
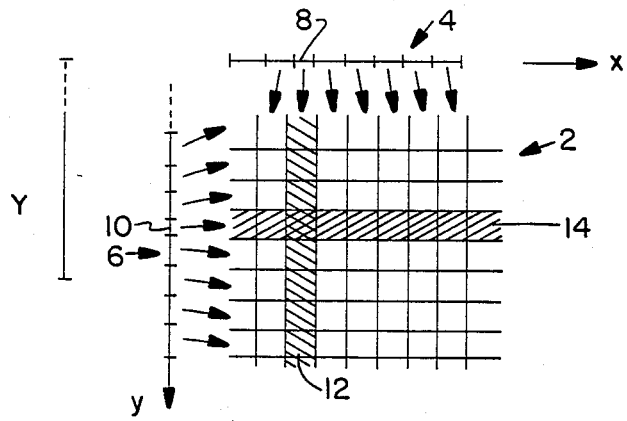

FIG. 1 shows a digital image 2 formed from a plurality of image points or picture elements arranged in array form. This image corresponds to a uniform radiation image received by a prior art radiation image formation device, whereof the position coder produces analog signals of coordinates X,Y, in which are then digitized by means of analog-digital converters having a differential non-linearity.

The characteristics of the analog-digital converters for the signals of coordinates X,Y have been represented respectively by numerical references 4,6. These characteristics associate a numerical value (digital image row or column number) with a signal of coordinate X,Y as a function of the amplitude of said digital.

If the analog-digital converters were perfect an amplitude range or segment of the same length would be allocated to each row or column of the digital image. However, a shorter segment 8,10 would contain less scintillations than the other segments (for a uniform radiation image), so that for the associated column 12 or row 14 there would be an intensity differing from that of the other rows and columns.

The invention aims at eliminating or at least greatly reducing such a defect. The invention relates to a nuclear radiation locating device as is diagrammatically shown in FIG. 2.

This locating device comprises a detection head 16 and a position coder 18. In per se known manner, the detection head generally comprises a collimator 20 having a plurality of parallel holes 22, so as to only receive a signal nuclear radiation 24, e.g. constituted by gamma photons coming from a given direction. This nuclear radiation is converted into photons or scintillations in a layer 26 of a NaI(Tl) crystal-type material. The photons are received in a plurality of photomultiplier tubes 28, each of which supplies an electric signal, called an electrical contribution, whose amplitude is a function of the location of the scintillations in the crystal.

Figure 3:
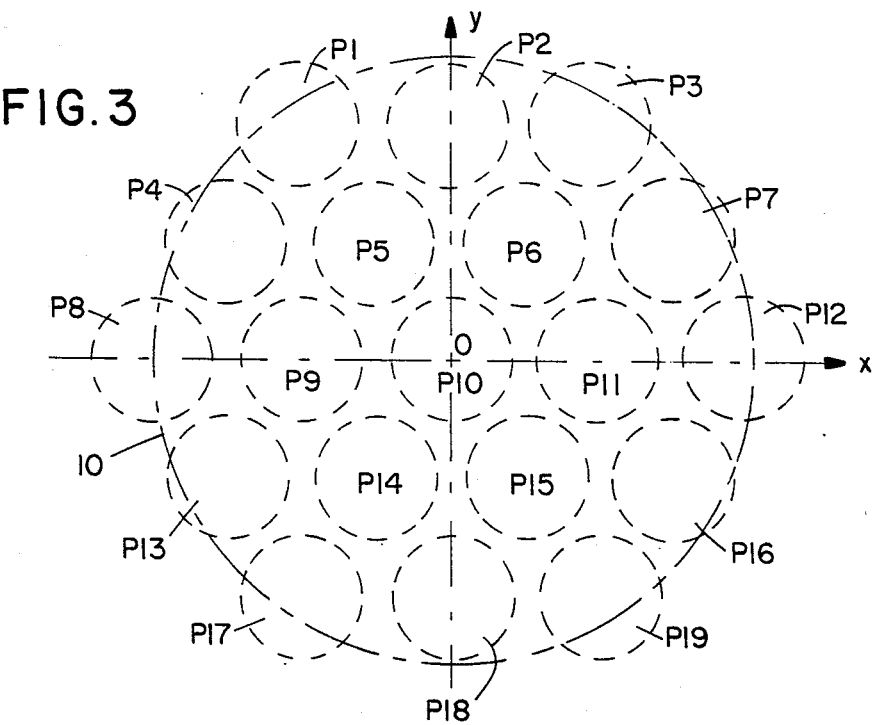
FIG. 3 is a plan view of the arrangement of photomultiplier tubes on the crystal of the detection head of a nuclear radiation locating device.

The photomultiplier tubes are arranged so as to cover in the optimal way the surface of crystal 26, as indicated in the plan view of FIG. 3. Each photomultiplier tube is surrounded by six photomultiplier tubes. The total number of photomultiplier tubes is generally 19,37,61 or 93, said number depending on the size of the photomultiplier tubes and the surface of the crystal.

Figure 2:
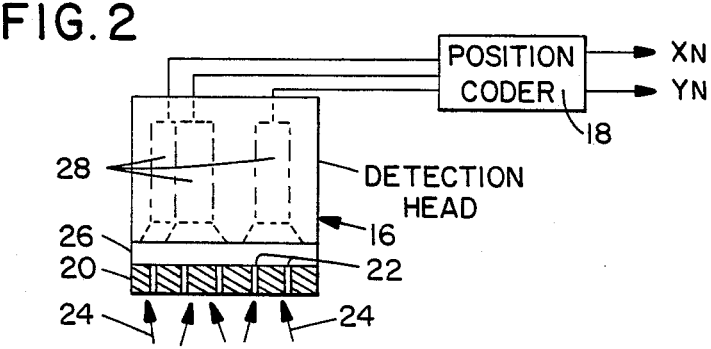

The electrical contributions of each photomultiplier tube are received by the position coder 18 (FIG. 2). In known manner (cf. U.S.-A-No. 3011057) sets of electrical resistors are used for producing analog signals $X^+$, $X^-$, $Y^+$, $Y^-$. Each set of resistors comprises one resistor per photomultiplier tube in whch the relative values of the resistors are a function of the position of the associated photomultiplier tube in a reference xOy generally centered on the center of the crystal (cf. FIG. 3).

Thus, the analog signals $X^+$, $X^-$, $Y^+$, $Y^-$ form weighted sums of the electrical contributions of the photomultiplier tubes.

A set of supplementary resistors can be used in which all the resistors have an identical value, in order to sum the electrical contributions of the photomultiplier tubes and in this way produce a signal Z representing the scintillation energy.

Figure 4:
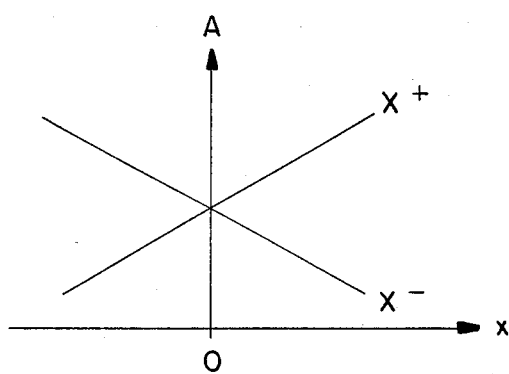
FIG. 4 is a graph illustrating the amplitude of the signals $X^+$, $X^-$ as a function of the position of the photomultiplier tube along axis Ox.

FIG. 4 is a graph of the amplitude A of the signals $X^+$ and $X^-$ as a function of the position of the scintillation along axis Ox. Signals $Y^+$ and $Y^-$ have an identical amplitude as a function of the position of the scintillation along axis Oy.

According to the invention, signals $X^+$, $X^-$, $Y^+$, $Y^-$ and possibly signal Z are firstly digitized and then combined to produce the digital coordinate signals X,Y. This makes it possible to more easily avoid or at least greatly reduce the visual display defects encountered in the prior art and mentioned with reference to FIG. 1.

The advantage resulting from the invention is due to the statistics of the energy of the gamma photons received by the crystal, which will now be explained relative to FIGS. 5 and 6.

Figure 5:
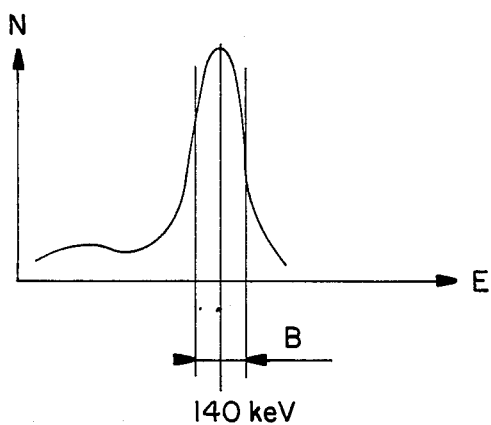
FIG. 5 is a histogram of the energy of a scintillation.

FIG. 5 is a histogram of the energy of the gamma photons received by the crystal. The theoretical energy of a gamma photon is 140 keV in the case where element $^{99}$Tc is used as the radioactive element. In practice, the energy of the gamma photon is located in a narrow band B centered on the theoretical energy and of midheight width approximately 10% of the value of the theoretical energy. A few low energy gamma photons are also emitted by Compton scattering.

This energy distribution of the gamma photons in band B implies that two photons, arriving at the same point on the crystal but having a different energy, would differently excite the photomultiplier tubes and would therefore produce different signals $X^+$, $X^-$ $Y^+$, $Y^-$. Therefore the same image point of coordinates X,Y could be obtained on the basis of different signals $X^+$, $X^-$, $Y^+$ and $Y^-$.

The statistical fluctuation performs a smoothing, which masks the possible differential non-linearity of the analog-digital converters.

Figure 7:
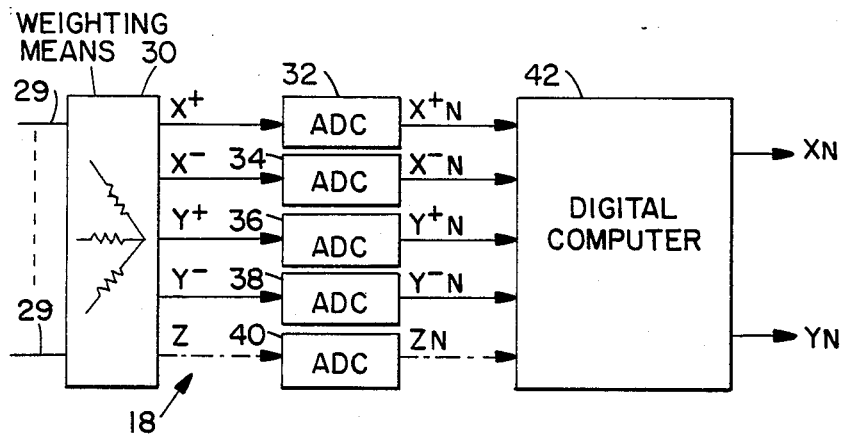
FIG. 7 is a block diagram of a position coder in accordance with a first embodiment of the invention.

The analog-digital conversion is diagrammatically illustrated in FIG. 7. Digital values expressed in binary form 00, 01, 10, 11, 100, 101 are associated with amplitude ranges represented by segments on an axis OA designating the amplitude of an analog signal. Value 10 is associated with a segment shorter than the other values in order to indicate a differential non-linearity of the analog-digital converter.

Figure 6:
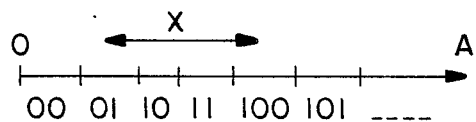
FIG. 6 shows the subdividing of an amplitude range into unequal segments for an analog-digital converter having a differential non-linearity.

The statistical fluctuation of the energy of the gamma photons has the consequence that the same pair of coordinates X,Y is obtained for a group of amplitudes of signals $X^+$, $X^-$, $Y^+$, $Y^-$, each group of amplitudes forming a range covering several ranges of the analog-digital converter, as shown for signal $X^+$ in FIG. 6.

The local defect represented by the short segment associated with value 10 is thus embedded in a longer segment created by the statistical fluctuation.

It has been experimentally found that the initial digitization of the signals $X^+$, $X^-$, $Y^+$, $Y^-$ according to the invention makes it possible to obtain with one-byte analog-digital converters a digital image with a quality comparable to that obtained in the prior art where the signals of coordinates X,Y are calculated in analog manner and then digitized using 12-bit analog-digital converters. Moreover, in the invention, there is a less marked differential linearity constraint. For example, experimental measurements have shown that the improvement of the linearity in the final image obtained could reach a factor of 20.

Therefore the invention makes it possible to significantly reduce the cost of the position coder part of a locating device or a radiation image formation device.

Figure 8:
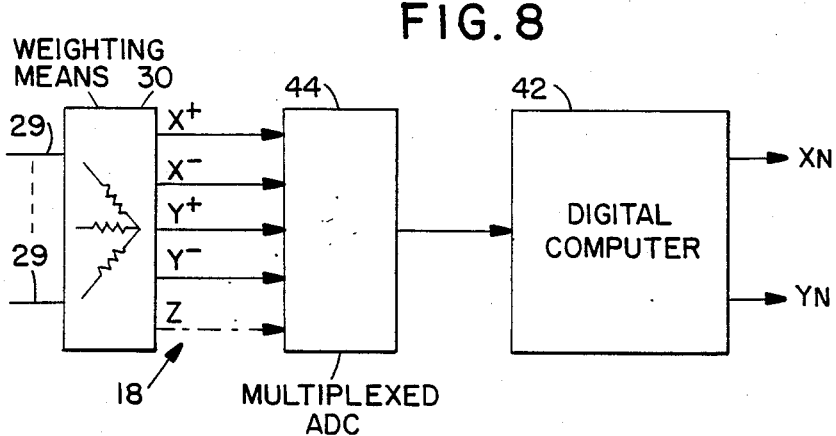
FIG. 8 is a block diagram of a position coder according to a second embodiment of the invention.

FIGS. 7 and 8 show embodiments of a position coder according to the invention.

The position coder 18 shown in FIG. 7 comprises a known weighting means 30, constituted by a plurality of resistors for supplying analog signals $X^+$, $X^-$, $Y^+$, $Y^-$ and possibly Z, as weighted sums of electrical contributions received from the photomultipliers by lines 29. The analog signals are then applied to the inputs of the analog-digital converters (ADC) 32, 34, 36, 38, 40, which supply the corresponding digital signals $X_N^+$, $X_N^-$, $Y_N^+$, $Y_N^-$ and $Z_N$.

These signals are received in a digital computer 42, where they are combined in order to produce digital signals of coordinates $X_N$, $Y_N$. The computer can be produced in any known manner, i.e. in the form of a group of logic circuits or in the form of a computer program.

The digital signal of coordinate $X_N$ is preferably produced in accordance with one of the following relations:

$$X_N = \frac{X_N^+ - X_N^-}{X_N^+ + X_N^-} \text{ or } X_N =$$

$$\frac{X_N^+ - X_N^-}{X_N^+ + X_N^- + Y_N^+ + Y_N^-} \text{ or } X_N = \frac{X_N^+ - X_N^-}{Z_N}$$

and symmetrically the signal of coordinate $Y_N$ is preferably produced according to one of the following relations:

$$Y_N = \frac{Y_N^+ - Y_N^-}{Y_N^+ + Y_N^-} \text{ or } Y_N =$$

-continued $$\frac{Y_N{}^+ - Y_N{}^-}{Y_N{}^+ + Y_N{}^- + X_N{}^+ + X_N{}^-} \text{ or } Y_N \frac{Y_N{}^+ - Y_N{}^-}{Z_N}$$

FIG. 8 illustrates a constructional variant of the digital coder, in which the plurality of analog-digital converters 32–40 is replaced by a single multiplexed analog-digital converter 44, which can be controlled in any known manner, particularly by a signal applied to a control input and specifying the selected input, or by a clock signal, which selects the inputs in a cyclic manner.

The weighting means 30 and the digital calculating means or computer 42 are functionally identical in FIGS. 7 and 8.

With reference to FIGS. 2 to 8 a nuclear locating device according to the invention has been described. The latter is often associated with an image formation means for forming a radiation image formation device, as shown in FIG. 9.

In FIG. 9, the digital signals of coordinates $X_N$, $Y_N$ supplied by locating device 46, in response to a nuclear radiation received, are transmitted to an image formation means or imager 48. The latter comprises a memory 50 for storing the number of radiations received at each image point, a readout 52 for displaying the image contained in the memory, an input-output circuit 54 for receiving the digital signals of coordinates $X_N$, $Y_N$ and a processing means 56 for controlling, by a channel 58, memory 50, readout 52 and input-output circuit 54.

Processing means 56 is designed to control the display on the readout 52 of an image contained in memory 50. It can also be designed in such a way as to carry out mathematical treatments on the images contained in memory 50, particularly with a view to obtaining tomographs.

The radiation image formation device or the radiation locating device may also comprise a visual display means 60, e.g. of the cathode-ray oscilloscope type, in order to display the position 62 of the image point corresponding to the pair of coordinates ($X_N$, $Y_N$) received. The display of an image point on the display means, or the taking into account in the memory of an image point is generally subject to a condition on the amplitude of the signal Z representing the scintillation energy.

We claim:

1. Device for locating a nuclear radiation incorporating a detection head for detecting a nuclear radiation and a position coder for locating said nuclear radiation, said detection head comprising a collimator, a planar layer of a material sensitive to said nuclear radiation for receiving on a first or front face a nuclear radiation transversing said collimator and for supplying on a second or rear face a light radiation which is a function of the nuclear radiation received, a plurality of transducers arranged on the rear face of said layer, each supplying an electric signal which is a function of the light radiation received, each nuclear radiation producing a light radiation seen by a plurality of transducers said locating device being characterized in that the position coder comprises weighting means for supplying analog electrical signals X+, X−, Y+, Y−, each representing weighted sums of the electric signals supplied by the transducers, the signlas X+, X− being a function of the position and the energy of the nuclear radiation received in accordance with an axis X and the signals Y+, Y− being a function of the position of the nuclear radiation received in accordance with an axis Y, a digitizing means for receiving the analog signals X+, X−, Y+, Y− and for supplying corresponding digital signals $X_N{}^+$, $X_N{}^-$, $Y_N{}^+$ and $Y_N{}^-$ and a calculating means or computer for determining the signals of digital coordinates $X_N$, $Y_N$ of the nuclear radiation received as a function of the digital signals $X_N{}^+$, $X_N{}^-$, $Y_N{}^+$ and $Y_N{}^-$.

2. Device according to claim 1, in which the digitizing means comprises a plurality of analog-digital converters, each of which processes one of the analog signals X+, X−, Y+, Y−.

3. Device according to claim 1, in which the digitizing means comprises a multiplexed analog-digital converter for sequentially processing the analog signals X+, X−, Y+, Y−.

4. Device according to claim 1, in which the calculating means or computer produces digital signals of coordinates $X_N$, $Y_N$ according to the relations:

$$X_N = \frac{X_N{}^+ - X_N{}^-}{X_N{}^+ - X_N{}^-} \text{ and } Y_N = \frac{Y_N{}^+ - Y_N{}^-}{Y_N{}^+ + Y_N{}^-}$$

5. Device according to claim 1, in which the computer produces digital signals of coordinates $X_N$, $Y_N$ according to the relations:

$$X_N = \frac{X_N{}^+ - X_N{}^-}{X_N{}^+ + X_N{}^- + Y_N{}^+ + Y_N{}^-} \text{ and } Y_N =$$

$$\frac{Y_N{}^+ - Y_N{}^-}{X_N{}^+ + X_N{}^- + Y_N{}^+ \, Y_N{}^-}$$

6. Device according to claim 1, in which the position coder also comprises a weighting means for supplying an analog signal of energy Z equal to the sum of the electric signals supplied by the transducers, said signal Z being converted into a digital signal $Z_N$ by the digitizing means of the position coder.

7. Device according to claim 6, in which the computer produces digital signals of coordinates $X_N$, $Y_N$ in accordance with relations:

$$X_N = \frac{X_N{}^+ + X_N{}^-}{Z_N} \text{ and } Y_N = \frac{Y_N{}^+ - Y_N{}^-}{Z_N}$$

8. Device according to claim 1 further comprising an image formation means comprising a memory, a readout and a processing means receiving said digital signals of coordinates $X_N$, $Y_N$, storing in said memory the number of nuclear radiations received at each image point of coordinates $X_N$, $Y_N$ and controlling the readout to produce a radiation image in which the intensity of each image point is a function of said number of received nuclear radiations.

* * * * *